(12) United States Patent
Humphrey et al.

(10) Patent No.: US 9,045,681 B2
(45) Date of Patent: Jun. 2, 2015

(54) REDUCED DRYING CARRIER FORMULATION

(75) Inventors: David Humphrey, Tullamarine (AU); Brett Skewes, Tullamarine (AU); Peter Cobham, Tullamarine (AU)

(73) Assignee: ARCH WOOD PROTECTION PTY LTD, Tullamarine, Victoria (AU)

( * ) Notice: Subject to any disclaimer, the term of this patent is extended or adjusted under 35 U.S.C. 154(b) by 0 days.

(21) Appl. No.: 13/980,463

(22) PCT Filed: Jan. 18, 2011

(86) PCT No.: PCT/AU2011/000058
§ 371 (c)(1),
(2), (4) Date: Sep. 30, 2013

(87) PCT Pub. No.: WO2011/085453
PCT Pub. Date: Jul. 21, 2011

(65) Prior Publication Data
US 2014/0031424 A1    Jan. 30, 2014

(51) Int. Cl.
| | |
|---|---|
| C09K 15/06 | (2006.01) |
| A01N 25/02 | (2006.01) |
| A01N 43/653 | (2006.01) |
| C08L 97/02 | (2006.01) |
| A01N 53/00 | (2006.01) |
| B27K 3/02 | (2006.01) |
| B27K 3/22 | (2006.01) |
| B27K 3/34 | (2006.01) |
| B27K 3/40 | (2006.01) |
| B27K 3/52 | (2006.01) |
| C08L 29/04 | (2006.01) |
| C08L 71/02 | (2006.01) |

(52) U.S. Cl.
CPC .............. *C09K 15/06* (2013.01); *A01N 25/02* (2013.01); *A01N 43/653* (2013.01); *B27K 3/0292* (2013.01); *B27K 3/22* (2013.01); *B27K 3/34* (2013.01); *B27K 3/343* (2013.01); *B27K 3/40* (2013.01); *B27K 3/52* (2013.01); *C08L 29/04* (2013.01); *C08L 71/02* (2013.01); *C08L 97/02* (2013.01); *A01N 53/00* (2013.01)

(58) Field of Classification Search
USPC .................................. 514/531; 252/364, 380
IPC ....................................................... C09K 15/06
See application file for complete search history.

(56) References Cited

U.S. PATENT DOCUMENTS

| | | | |
|---|---|---|---|
| 3,547,679 A | 12/1970 | Moren | |
| 4,615,737 A * | 10/1986 | Kiisler et al. | 106/12 |
| 4,923,760 A | 5/1990 | Adkins et al. | |
| 5,817,369 A * | 10/1998 | Conradie et al. | 427/389.9 |
| 6,572,788 B2 * | 6/2003 | Walker | 252/380 |
| 2002/0094937 A1 | 7/2002 | Hirsbrunner et al. | |
| 2007/0021385 A1 * | 1/2007 | Zhang et al. | 514/63 |

FOREIGN PATENT DOCUMENTS

| | | |
|---|---|---|
| GB | 600961 A | 4/1948 |
| GB | 814584 A | 6/1959 |
| GB | 2271579 A | 4/1994 |
| WO | 01/34355 A2 | 5/2001 |
| WO | 2006/091113 A1 | 8/2006 |
| WO | 2008/026941 A1 | 3/2008 |

* cited by examiner

*Primary Examiner* — Rei-Tsang Shiao
(74) *Attorney, Agent, or Firm* — Lucas & Mercanti, LLP

(57) ABSTRACT

According to the present invention there is provided a carrier formulation adapted to operatively support a preservative or preservative mixture within a material for treating wood, said carrier formulation comprising water and one or more water-miscible, water-soluble or water-emulsifiable compounds wherein said carrier formulation provides for preservative penetration and substantial preservative retention within the treated wood; and wherein the treated wood requires relatively little post-treatment drying. The carrier formulation provides for substantially complete or envelope penetration of the preservative within the treated wood.

24 Claims, 1 Drawing Sheet

REDUCED DRYING CARRIER FORMULATION

CROSS-REFERENCE TO RELATED APPLICATION

This application is a 371 of PCT/AU2011/000058, filed Jan. 18, 2011, the contents of which are incorporated herein by reference.

FIELD OF THE INVENTION

The present invention relates to the treatment of wood products with a preservative formulation. More specifically, the invention relates to the treatment of wood with a preservative material comprising a carrier comprised of water and one or more water-miscible, water-soluble and/or water-emulsifiable compounds. Moreover, the carrier provides either for complete penetration of the preservative material within the wood, or for incomplete, envelope-like penetration of preservative into the wood.

The invention has been developed primarily as an aqueous formulation for the treatment of timber suitable for above-ground, interior building and structural applications in exterior, above-ground situations. Although the invention will be described hereinafter with reference to these applications, it will be appreciated that it is not limited to this particular field of use.

BACKGROUND OF THE INVENTION

Any discussion of the prior art throughout the specification should in no way be considered as an admission that such prior art is widely known or forms part of the common general knowledge in the field.

Wood is a staple construction material used throughout the world. However, it is prone to degradation from elements including the natural environment, weather events, insects, rot and fire. Accordingly, a range of chemical treatments has been developed to improve the durability and working lifetime of wooden structures.

To treat and prevent infestations, timber is often impregnated with a preservative such as a fungicide or insecticide. The preservative is typically present in a carrier, with the mixture being applied to the surface of the timber, for example by dipping, spraying, brushing or pressure treatment, such that the carrier and preservative are absorbed in to the timber.

The treatment of timber or timber products with preservative compounds involves the introduction of stable chemicals into the cellular structure of the timber. This, in turn, protects the timber from hazards such as fungi, insects and other wood-destroying organisms. Preservative treatments may also include the introduction of chemicals that improve resistance to degradation by fire.

Preservative treatment of wood is often carried out at increased pressure so as to force the liquid preservative solution into the pores of the wood. A vacuum may be applied prior to the introduction of the treatment solution in order to increase penetration. The active chemical agent is usually dissolved in a solvent (e.g. a "carrier") and the preservative solutions are generally of relatively low viscosity in order to facilitate the penetration of the treatment solution.

Increased penetration of the preservative solution can also be achieved by diffusion, which despite involving less expensive equipment, requires a longer time period and greater levels of stock holding. Diffusion time is also influenced by the initial wood moisture content, especially when dealing with aqueous carriers.

TABLE 1

Minimum H3 preservative retention in the penetration zone
Waterborne
Light organic solvent preservatives

| CCA | Cu + DDAC | Copper azole | Creosote | TBTN or TBTO | Propiconazole + Tebuconazole | Copper naphthenate | Synthetic Pyrethroids |
|---|---|---|---|---|---|---|---|
| 0.380 | Soft: 0.35<br>Hard: 0.39 | 0.229 | 8.00 | 0.080<br>0.160 | Soft: 0.06<br>Hard: __ | 0.100 | .02 Permethrin<br>.03 Cypermethrin<br>.002 Deltamethrin<br>.0047 Bifenthrin |

In Australia, the treatment of timber is covered by the Australian Standard "AS 1604-2010" series. Hazard Class H3 is defined as being for protection against "moderate fungal decay and termite hazard for decking, fascia, cladding, window reveals, and exterior structure timber". The timber is exposed to the weather or not fully protected. It is clear from the ground and the area is well drained and ventilated. H3 treatment is designed to prevent attack by insects, including termites, and decay. Hazard Class H4 defines "severe decay, borers and termites, fence posts, greenhouses, pergolas (in ground and landscaping timbers". The timber is in contact with the ground or is continually damp so there is a severe decay hazard. The treatment stops attack by insects, including termites, and severe decay. Retention is measured in mass/mass (% m/m).

"Penetration" is defined under the H3/H4 Standards as: "All preservative-treated wood shall show evidence of distribution of the preservative in the penetration zone in accordance with the following requirements: (a) If the species of timber used is of natural durability class 1 or 2, the preservative shall penetrate all the sapwood. Preservative penetration of the heartwood is not required; (b) If the species of timber used is of natural durability class 3 or 4, the preservative shall penetrate all of the sapwood and, in addition one of the following requirements shall apply; (i) Where the lesser cross-sectional dimension is greater than 35 mm, the penetration shall be not less than 8 mm from any surface. Where the lesser cross-sectional dimension is equal or less than 35 mm, the penetration shall be not less than 5 mm from any surface; (ii) Unpenetrated heartwood shall be permitted, provided that it comprises less than 20% of the cross-section of the piece and does not extend more than halfway through the piece from one surface to the opposite surface and does not exceed half the dimension of the side in the cross-section on which it occurs".

In order to provide for penetration of the preservative, a carrier must be used. As shown in the Australian Standards, the carriers presently available can be characterised broadly as "water-borne" or "solvent-borne" systems.

A carrier must be capable of providing sufficient penetration of the preservative into the wood, thereby to provide an effective barrier against infestation. Other considerations in the choice of carrier include the desired rate of penetration, cost, environmental, health and safety considerations. A carrier may provide for a "complete penetration" formulation, or for "incomplete penetration", often referred to as an "envelope treatment" in which one or more preservatives penetrate only partially the cross section of the timber in question.

The preservatives commonly used in timber treatment can be characterised according to the carrier vehicle used to carry preservatives into the timber, and by the active chemicals protecting against the various hazards. The final step in the preservation process is that the solvent must then be removed before the timber is made available for use.

Inorganic boron compounds have been used to protect the sapwood of susceptible hardwoods against lyctid or "powder post" borers. Such treatment consists of soaking freshly-sawn unseasoned timber in solutions of boron salts. The salts diffuse through the timber, thereby treating it, and after such treatment, the timber is allowed to dry. However, boron salts are readily soluble in aqueous solutions and can be leached relatively easily from the wood once treated. This largely restricts boron-treated timber to interior uses such as flooring or joinery, wherein it is protected from the external environment.

Copper, chromium and arsenate ($H_2AsO_4^-$), "CCA", is a leach-resistant preservative that has been used to treat solid wood in external applications. CCA impregnates the timber in a water/salts carrier and reacts with the wood cell components so that the active elements are "fixed" into the wood's structure. The arsenic component protects the sapwood from insect attack; the copper and arsenic protect against degradation due to fungi; whilst the chromium chemically locks the elements into the timber, offering a relatively high resistance to leaching. Following such treatment, the timber must be re-dried. This process can decrease the strength of the timber, and invariably adds to the cost. However, due to environmental health and safety issues, CCA is coming under increasing regulation and is thus becoming a less desirable treatment from both commercial and environmental standpoints.

Light Organic Solvent-borne Preservatives (LOSPs) comprise a light organic solvent, typically white spirits, to carry the preservative into the timber. White spirits is a mixture of saturated aliphatic and alicyclic $C_7$-$C_{12}$ hydrocarbons with a w/w content of about 15-20% aromatic $C_7$-$C_{12}$ hydrocarbons. The solvent is drawn out in the final stages of treatment, with the preservative remaining within the wood. Such preservatives are typically fungicides, having copper, tin, zinc, azoles and pentachlorophenols (PCPs) as major toxicants. Synthetic pyrethroids such as permethrin may be incorporated within the preservative composition if an insect hazard is also present. One principal advantage of LOSP treatment is that the treated timber does not swell, making such treatment quite suitable for "finished" items such as mouldings and joinery. The majority of LOSPs used in wood treatment also contain insecticides and/or waxes so as to give the surface water repellent properties. However, odour and exposure to VOCs (volatile organic compounds) are significant environmental/occupational health and safety issues. Accordingly, whilst effective, LOSP treatments are becoming increasingly undesirable.

Alkaline Copper Quat (ACQ) contains copper and a quaternary ammonium compound. It is used to protect timber against decay, fungi and insects. ACQ is applied as a water-borne preservative using an external pressure process and is suitable for external timber applications.

Copper azole can be used in water-borne pressure treatment processes. It is a preservative that contains copper, boric acid and tebuconazole. Copper azole has been used in Australia as a replacement for CCA for treatments having external applications.

A range of synthetic pyrethrins and pyrethroids has also been developed for use in treating timber. Many such formulations employ similar chemicals to those used in flea collars for dogs and cats or for fly sprays. Accordingly, such chemicals are already generally well received in the community. However, as preservatives in an aqueous solvent for the treatment of timber, such components are still susceptible to leaching from the timber after treatment. Moreover, swelling of the timber after treatment due to water retention is a significant detriment.

Creosote and PEC (pigment emulsified creosote) are commonly used oil-borne preservatives that are painted onto timber surfaces, but can also be applied in a pressure-based process for better penetration. These compounds have volatile components and hence, a characteristic odour. This makes creosote and PEC only really suitable for use in external or industrial applications.

U.S. Pat. No. 5,846,305 discloses a liquid wood preservative solution including copper metal, liquid amine solvent, a boron compound and a glycol. Glycol has been used as a replacement for water in ancient timber restoration, or for dimensional stability in a technique known as "bulking" for many years. Boron is highly miscible in glycol and thus the movement of a glycol/boron solution into the wood is due to diffusion. Due to the length of time required for adequate diffusion into the wood, this type of preservative requires vacuum pressure application and is thereby unsuitable for the more preferred application methods such as brushing, dipping or spraying.

As the use of water-based carriers has been found to increase the moisture content of the timber, resulting in undesirable swelling of the wood, and necessitating a further drying processes after treatment, many current methods of treating and protecting wood typically rely on using a solvent.

One such composition for the treatment of timber is Tanalith-T (U.S. Pat. No. 7,361,215, to the present Applicant). "Tan-T" uses linseed oil in combination with a high flash solvent carrier to transport a preservative into the wood. This promotes the formation of a well-defined "envelope" of preservative, thereby treating and preventing infestations of termites and other insects. However, with the increasing cost of both vegetable (i.e. "drying") and mineral oils, there remains a need for the development of other carriers that can provide a protective envelope similar to that of the presently-used vegetable oil/mineral oil carrier formulations, whilst preferably minimising the increase in moisture content of the timber as a result of the treatment, and without need for further drying steps.

WO 02/081159 relates to a method for the protective treatment of wood by thermal treatment at 60-250° C. and additional treatment using an amine and/or amine derivative and/or salt thereof. The treated wood has good resistance even to harmful organisms. The method is carried out without compounds containing heavy metals and wood treated in this way has no impact on the environment. However, it will be appreciated that the initial heat-treatment step is relatively undesirable for cost-energy reasons.

NZ 543124 relates to a process for treating dimensioned wood, dimensioned lumber or dimensioned timber or veneer or particle based products or reconstituted wood products or other cellulosic materials, the said process comprising impregnating the timber or product to its core using a pressure differential or pressure differentials over one or more composition exposure time/s, wherein the composition to which the timber or product is exposed for uptake is a liquid based composition having a biocidal and/or preservative action, and wherein the liquid based composition is at least primarily water based but content does include one surfactant or at least one other liquid (i.e. includes (i) a glycol content or (ii) a glycol content and a surfactant or wetting agent content) and wherein the liquid uptake us less than 80 L/m$^3$.

It is an object of the present invention to overcome or ameliorate at least one of the disadvantages of the prior art, or to provide a useful alternative.

Despite the many and varied techniques for the treatment of wood, there remains a need to satisfy the "dry after" requirement for structural treated timber, having less than 15% moisture content, whilst achieving the required penetration of active compounds into the wood.

Additionally, remains a need for a material for treating wood that has relatively low odour, relatively minimal VOC emissions, and relatively less reliance on mineral spirits, whilst at once providing relatively good dimensional stability to the treated wood.

As applied in the context of the present invention, "miscibility" is the property of liquids to mix in all proportions, forming a homogeneous solution. Water and ethanol, for example, are miscible since they mix in all proportions. By contrast, substances are said to be "immiscible" if in some proportion, they do not form a solution, e.g. diethyl ether/water. Moreover, the terms "not miscible" and "immiscible" are taken to be synonymous.

By "operatively support", as it appears within the claims is intended to mean that the carrier enables the preservative to perform its function within the wood. In other words, the carrier enables the preservative to migrate to its operational extent (i.e., envelope or complete penetration).

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

Although the invention will be described with reference to specific examples it will be appreciated by those skilled in the art that the invention may be embodied in many other forms.

SUMMARY OF THE INVENTION

According to a first aspect of the present invention there is provided a carrier formulation for operatively supporting a preservative or preservative mixture within a material for treating wood, said carrier formulation comprising water and one or more water-miscible, water-soluble and/or water-emulsifiable compounds wherein said carrier formulation provides for preservative penetration and substantial preservative retention within the treated wood; and wherein said carrier formulation provides for treated wood that requires relatively reduced drying. However, for mixtures, the non-water components may not all be water-miscible when mixed with water individually, but when used together they become miscible.

In an embodiment, said preservative penetration within said treated wood is by way of substantially complete penetration.

In another embodiment, said preservative penetration within said treated wood is by way of an envelope of preservative to specified predetermined depth from the surface of said wood. In an especially preferred embodiment, this depth is at least about 5 mm.

In an embodiment, carrier remains inert and minimises the moisture content increase of said wood. In an embodiment, said moisture content increase of said wood is from about 3% to about 5% w/w. In another embodiment, the moisture content may increase by about 10%, but then through minimal drying the wood returns to a "dry after" moisture content.

In an embodiment, said one or more water-miscible compounds are selected from the group consisting of: glycerol, propylene glycol, ethylene glycol and the like, and mixtures thereof glycols, amine oxides, quaternary ammonium compounds, glycol ethers, esters, alcohols, phenols, diols, triols, ketones, carbamates, amides, sulfoxides, amines, acids (e.g. amino acids), modified cellulosics or the like, or combinations thereof, polymer/resins (e.g. polyvinyl alcohol), PEGs, water dispersible alkyds, polyesters, proteins, etc.

In an embodiment, said one or more water-miscible compounds are ethylene glycol or propylene glycol.

In an embodiment, the ratio of water to one or more water-miscible compounds present in the carrier is within the range of about 1:99 to about 99:1. In an embodiment, the ratio of water to one or more water-miscible compounds present in the carrier is within the range of about 5:95 to about 95:5 w/w. In an embodiment, the ratio of water to one or more water-miscible compounds present in the carrier is within the range of about 10:90 to about 90:10 w/w. In an embodiment, the ratio of water to one or more water-miscible compounds present in the carrier is within the range of about 20:80 to about 80:20 w/w. In an embodiment, the ratio of water to one or more water-miscible compounds present in the carrier is within the range of about 30:70 to about 70:30 w/w. In an embodiment, the ratio of water to one or more water-miscible compounds present in the carrier is within the range of about 40:60 to about 60:40 w/w. In an embodiment, the ratio of water to one or more water-miscible compounds present in the carrier is about 50:50 w/w.

In an embodiment, said carrier enters the cell walls of said wood thereby limiting further swelling of said wood following treatment of said wood with said preservative mixture.

In an embodiment, said treated wood is classifiable in the art as "dry after" (moisture content<15% w/w) following treatment with said preservative mixture. In an embodiment, said treated wood is substantially not susceptible to leaching of said preservative from said wood.

In an embodiment, said treated wood has relatively constant dimensional stability as a result of said carrier remaining within the cells of said treated wood. In an embodiment, said treated wood does not require a subsequent drying operation.

In an embodiment, the uptake of said carrier by said wood is less than 200 L/m$^3$. In an embodiment, the uptake of said carrier by said wood is less than 100 L/m$^3$. In an embodiment, the uptake of said carrier by said wood is less than 80 L/m$^3$. In an embodiment, the uptake of said carrier by said wood is in the range of about 5 to 30 L/m$^3$. In an embodiment, the uptake of said carrier by said wood is in the range of about 15 to 25 L/m$^3$. In an embodiment, the uptake of said carrier by said wood is less than about 20 L/m$^3$.

In an embodiment, said formulation is applicable to hardwood and/or softwood species. In an embodiment, the formulation is applicable to wood composites selected from the group consisting of: particle board, plywood, laminated veneer lumber (LVL), medium density fibreboard (MDF) and oriented strand board (OSB).

According to a second aspect of the present invention there is provided a material for treating wood, said material comprising a preservative or preservative mixture and a carrier formulation defined according to the first aspect of the present invention.

In an embodiment, the material comprises below about 5% w/w preservative content. In an embodiment, the material comprises below about 2% w/w preservative content. In an embodiment, the material comprises below about 1% w/w preservative content. In an embodiment, said preservative or preservative mixture is not miscible in said material. In an embodiment, said preservative or preservative mixture is miscible in said material. In an embodiment, said preservative or preservative mixture is sparingly or partially miscible in said material.

In an embodiment, said preservative or preservative mixture is solubilised in said carrier formulation using a co-solvent. In an embodiment, said preservative or preservative mixture is formulated within said carrier formulation as an emulsion. In an embodiment, said preservative or preservative mixture is chemically stable in said carrier formulation.

In an embodiment, said preservative or preservative mixture is present in unmodified or modified form. In an embodiment, said modified form comprises a chemical modification providing relatively increased stability against environmental conditions such as heat and/or chemical degradation.

In an embodiment, said modified form is a microencapsulated form and/or a micronised form.

In an embodiment, said preservative or preservative mixture penetrates said wood to the degree required in order for the said wood to function in the manner intended. In an embodiment, said preservative or preservative mixture is selected from the group consisting of: insecticides, termiticides, fungicides, mouldicides, or the like, and mixtures thereof.

In an embodiment, said preservative or preservative mixture is selected from the group consisting of: synthetic pyrethroids (such as allethrin, bifenthrin, cypermethrin, cyphenothrin, deltamethrin, permethrin, prallethrin, resmethrin, sumithrin, tetramethrin, tralomethrin, transfluthrin, imiprothrin), triazoles, triazoles, copper azole-based compounds, organic biocides, thiachloprid, imidachloprid or the like, and mixtures thereof, triazoles, copper azole-based compounds, organic biocides, iodopropynylbuthylcarbamate (IPBC), organic tin compounds such as tributyltin naphthenate (TBTN), organic copper compounds such as copper 8 quinolinolate, copper naphthenate, organic zinc compounds, quaternary ammonium compounds, tertiary ammonium compounds, isothiazolones, boron compounds, 3-benzothien-2-yl-5,6-dihydro-1,4,2-oxathiazine-4-oxide (Bethogard®) and bis-(N-cyclohexyldiazenuimdioxy) copper ("Cu—HDO")", and mixtures thereof.

In an embodiment, said preservative or preservative mixture comprises bifenthrin, permethrin, tebuconazole, propiconazole, or a combination thereof.

In an embodiment, said preservative or preservative mixture comprises copper naphthenate, or a mixture thereof.

In an embodiment, said preservative or preservative mixture is selected from the group consisting of: organochlorine compounds, organophosphates, neonicotinoids and biological insecticides. In an embodiment, said neonicotinoids are selected from the group consisting of: acetamiprid, clothianidin, dinotefuran, imidacloprid, nitenpyram, thiacloprid, thiamethoxam and mixtures thereof.

In an embodiment, the preservative content present in the material is sufficient to give retention values to meet Australian Hazard Level 2 (H2 or H2F) 3 and 4 (H3 and H4) treatment requirements.

In an embodiment, to said material is added, alone or in combination, colour/s, water repellents, mouldicides, termiticides, co-solvents, and the like.

According to a third aspect of the present invention there is provided a method of treating wood, said method comprising the step of contacting said wood with a material defined according to the second aspect of the present invention. In an embodiment, said step of contacting said wood is performed by means selected from the group consisting of: pressure application, spraying, dipping, rolling, painting, or any combination thereof.

According to a fourth aspect of the present invention there is provided treated wood, when so-treated by a method defined according to the third aspect of the present invention.

According to a fifth aspect of the present invention there is provided a method of formulating a material for treating wood, said method comprising the step of admixing a preservative or preservative mixture, water and a water-miscible carrier.

According to a sixth aspect of the present invention there is provided a material for treating wood, when formulated by a method defined according to the fifth aspect of the present invention.

It will be appreciated by those skilled in the art that to the inventive formulation can readily be added, alone or in combination, colour/s, water repellents, mouldicides, termiticides, co-solvents, etc.

BRIEF DESCRIPTION OF THE FIGURES

A preferred embodiment of the invention will now be described, by way of example only, with reference to the accompanying drawings in which.

PREFERRED EMBODIMENT OF THE INVENTION

Figure 1:
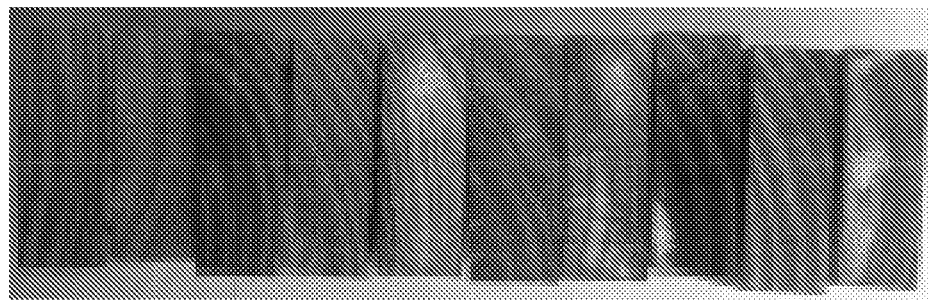
FIG. 1 is a photographic image of cross-section of samples treated in Example 1b, after cutting and application of a copper spot rest reagent. The dark green/black coloration indicates the presence of copper.

The present invention will now be described in relation to the treatment of wood with non water-miscible preservatives, such as pyrethroids, and azoles, in a water/water-miscible carrier formulation. Although the invention will be described with reference to specific examples, it will be appreciated by those skilled in the art that the invention may be embodied in many other forms.

The present invention provides a material for the treatment of wood including a water-miscible carrier to deliver an active chemical species, such as one or more preservatives, into the timber. The delivery may be characterised according to "complete" or "envelope" penetration depending upon the choice of carrier, the choice of preservative or the method of applying the carrier to the wood. The present invention may address one or more of the negative cost and environmental effects associated with the present preservative treatments such as LOSPs. For instance, LOSPs use non-polar organic solvents, such as white spirit, resulting in problems such as high levels of odour and VOCs. The present invention is designed to mimic the "dry after" nature of LOSPs whilst substantially ameliorating the negative effects.

In one embodiment, the invention provides a material for treating wood including a water-miscible carrier formulation, preferably propylene or ethylene glycol, in a water:glycol ratio of 40:60, 30:70, 20:80, 10:90, or 5:95% w/w. In a preferred embodiment, the ratio is about 50:50% w/w. In another preferred embodiment, the ratio is 60:40, 70:30, 80:20, 90:10, 95:5, or 99:1% w/w. It is intended that all ratios within such limits are encompassed by the above figures (e.g. 23:77, 82:18, etc.). The preservative ratio in this material is sufficient to provide the minimum retention levels of the preservative in the wood to AS1604 series requirements as defined previously.

The preservative can be present in unmodified or modified form. The modified form may comprise a chemical modification providing relatively increased stability against environmental conditions such as heat and/or chemical degradation. In an especially preferred embodiment, the modified form is a microencapsulated form and/or a micronised form.

The preservative present in the formulation of the present invention can include an insecticide, termiticide, fungicide, mouldicide, or the like, or mixtures thereof. More preferably, the preservative is selected from the non-exhaustive group consisting of synthetic pyrethroids, triazoles, quaternary ammonium compounds, copper azole-based compounds, organic biocides and mixtures thereof, generally excluding the use of boron as a sole biocide. Most preferably, the preservative is a synthetic pyrethroid such as bifenthrin or permethrin, or an azole or mixture of azoles such as propiconazole, tebuconazole or cyproconazole, or a quaternary ammonium salt such as didecyl-dimethylammonium chloride, or mixtures thereof.

The pyrethroids, azoles and other organic biocides formulated as preservatives in the material of the present invention are optionally formulated into the water/glycol formulations as an emulsion or using a co-solvent.

The material of the present invention can be applied to the wood by a wide range of methods, such as pressure application, spraying, dipping, rolling, painting, or combinations thereof. The material is preferably applied by brushing, dipping and spraying to enable efficient penetration of the material into the wood.

The inventive material can also be applied to all relevant species of wood, i.e. hardwood and softwood, as well as engineered wood products such as plywood, laminated veneer lumber, oriented strand board, particleboard and medium density fibreboard (either before or after manufacture). Most preferably, the material is applicable to pine used in household decking. The uptake of the preservative formulation by the wood being treated is expectably less than about 200 $L/m^3$, more preferably less than about 100 $L/m^3$, more preferably still, less than about 80 $L/m^3$.

The Applicant has found that water and water-miscible solvents such as glycol can be used to closely mimic wood treatment processes with non-polar solvents such as LOSPs.

Surprisingly, active compounds used in wood treatment applications that are generally considered immiscible or to have very low solubility in water (e.g. bifenthrin) are found to be sufficiently penetrated into wood with the inventive water-based formulation. Whilst actives such as boron are completely miscible in glycol/water solutions, highly diffusible and are thus expected to penetrate into the wood, non diffusible actives such as pyrethroids and azoles have been found by the Applicant to penetrate into the wood. Moreover, penetration of the actives into the wood has been observed even where there is no evidence of carrier penetration into the wood.

The non water-miscible actives, when formulated into the material of the present invention, have also been shown to be stable in the water-based formulation. Without wishing to be bound by theory, it is thought that the mechanism of penetration of the inventive material is other than by diffusion; the moisture content of the untreated wood is generally not sufficient to promote diffusion. Further, the penetration mechanism is also not thought to be via water penetration as there is insufficient water in the untreated wood to fill the cell structure. The water and non-water component of the carrier system, when used together, facilitate penetration of the preservative actives.

Depending upon the ratio of water:glycol in the formulation, which is preferably about 1:99, 5:95, 10:90; 20:80, 30:70, 40:60, 50:50, 60:40, 70:30, 80:20, 90:10, 95:5 or 99:1% w/w, the moisture content increase of the wood can be limited to between around 3 to 5% w/w. The water-miscible carrier (e.g. glycol) acts as an inert agent and limits moisture content increase. The glycol, as is known from the art, further acts as a "bulking" agent that enters the cell wall and gives relatively "permanent" swelling of the wood and a reasonable level of dimensional stability.

Further, water causes swelling of the cell structure of the wood through chemical bonding with the cellulose fibres, thereby forcing them apart. Such swelling is largely reversible as the wood dries, but nonetheless requires significant energy. Further, such reversibility occurs generally only below the fibre saturation point. Glycols are also known to swell wood. However, such swelling is deemed to be "permanent" as the energy required to reverse this chemical bonding with glycols is excessively large.

Again without wishing to be bound by theory, it is thought that once the glycol molecules have bonded with the cellulose fibres ("enabled" swelling of the wood) it is much less likely to leach, compared with glycol added in excess of the fibre saturation point. Fibre saturation in wood occurs at about 30% w/w moisture content. The swelling of wood treated with glycol is greater than that occurring with the same amount of water simply due to the respective molecular sizes.

Whilst the treatment of wood with glycols is well known in the art, the only biocide that has been included with such treatment is boron. Boron is highly miscible in water/glycol and thus the movement of the glycol/boron solution into the wood is due to diffusion. However, due to the length of time required for diffusion into the wood, this type of preservative is required to be forced into the wood by vacuum pressure. By contrast, it has been shown that the present invention allows the treatment of wood with a wide variety of preservatives including non water-miscible actives, such as pyrethroids and azoles, in a relatively cheap, non-toxic and non environmentally-damaging form though the use of simple, convenient methods such as brushing, dipping or spraying.

It will be appreciated that the illustrated water-based material used in the treatment of wood achieves required penetration of the wood with non-water-miscible actives that are stable in the water-based formulation while also being relatively non-toxic and relatively environmentally-friendly.

It will be further appreciated that the inventive material substantially overcomes or ameliorates many of the disadvantages inherent in using known water-based carriers. These operational advantages are due to the "permanent" swelling of the wood by the glycol carrier such that leaching of the actives out of the wood is largely avoided, a re-drying step is not necessary, and the dimensional stability of the treated wood is maintained.

Although the invention has been described with reference to specific examples it will be appreciated by those skilled in the art that the invention may be embodied in many other forms.

EXAMPLES

The following examples are intended to be representative only, and not limiting of the present invention.

Examples of Complete Penetration

Example 1a

In this example, the patented (see, AU 1992023797) Tanalith® E concentrate containing copper and tebuconazole, was diluted with ethylene glycol and water. The formulation was subjected to accelerated storage stability testing (+54° C./2 weeks & 0° C./1 week), and by chemical analysis was shown to be stable under both sets of conditions. The ethylene glycol content could be varied between 0 and 80% and the formulation remained stable.

| Component | % w/w |
|---|---|
| Tanalith ® E concentrate | 16 |
| Ethylene glycol | 50 |
| Water | 34 |

Example 1b

The use of a reduced drying formulation to treat radiata pine decking is illustrated in Example 1b. Satisfactory treatment was obtained, and no redrying was required. The preservative/carrier formulation was as per Example 1a, above.

Substrate: Kiln dried radiata pine sapwood (dressed all round), 70×25 mm. Ten replicates, end sealed.

Treatment: Flood, +80 kPa (3 min), drain, vacuum (−85 kPa, 20 min).

Mean uptake: 87 L/m$^3$.

Moisture content: 15.8%

Penetration: >90% (as judged by application of a copper spot test, refer to FIG. 1).

Volumetric swelling: 3.2%

Example 1c

In this example, carriers other than ethylene glycol are used. Accordingly, Tanalith® E concentrate containing copper and tebuconazole, was diluted with a water-miscible co-solvent and water (refer to formulation composition in Table 2, below). For comparison, matched samples of radiata pine (90×45 mm) were treated with Tanalith® E concentrate diluted with water only, using a full cell process (sample 1c(i)) and a low uptake process (sample 1c(ii)). The uptakes were 215 and 86 L/m$^3$, respectively for the water-only dilutions. The high uptake process gave satisfactory penetration, whereas the low uptake process did not. The reduced drying formulations (samples 1c(iii) and 1c(iv)) however gave satisfactory penetration at similar low uptakes. For both of the latter formulations, the moisture content (MC) of the treated specimens was less than 17%.

TABLE 2

Data obtained from Example 1c

| Sample No. | Formulation Composition (% w/w) | | | Measurements | | | |
| | Tan ® E | Water | Co-solvent | Uptake (L/m$^3$) | Pen. (%) (Pass/Fail) | MC (%) | Swell (%) |
|---|---|---|---|---|---|---|---|
| 1c(i) | 3.7 | 96.3 | — | 215 | 100 (P) | 46 | 9.1 |
| 1c(ii) | 17.9 | 82.1 | — | 86 | 85 (F) | 24 | 5.3 |
| 1c(iii) | 16 | 34 | Glycerol 50 | 73 | 90 (P) | 16 | 2.6 |
| 1c(iv) | 17.5 | 33 | PG 49.5 | 91 | 90 (P) | 16.8 | 6.4 |

Note:
PG = 1,2-propylene glycol; Penetration ≥90% = pass, <90% = fail; Swell = volumetric swelling; Low uptake process = flood, +80 kPa (3 min), drain, −85 kPa final vacuum (20 min).

Example 1d

The azoles tebuconazole and propiconazole may also be formulated into a reduced drying carrier system. In this example, the azoles were introduced in the form of an emulsifiable concentrate (Wolman AG, 10% w/w azoles), which was diluted with water and ethylene glycol.

| Component | % w/w |
|---|---|
| Wolman ® AG concentrate | 9.1 |
| Ethylene glycol | 40.4 |
| Water | 44.2 |
| Azole marker (proprietary) | balance |

Substrate: Kiln dried radiata pine sapwood (rougher headed), 90×35 mm. Ten replicates, end sealed.

Treatment: Flood, +80 kPa (1 min), drain, vacuum (−85 kPa, 15 min).

Mean uptake: 54.1 L/m$^3$.

Moisture content: 17.8%

Penetration: 90% (as judged by application of a spot test).

Volumetric swelling: 2.5%

Figure 2:
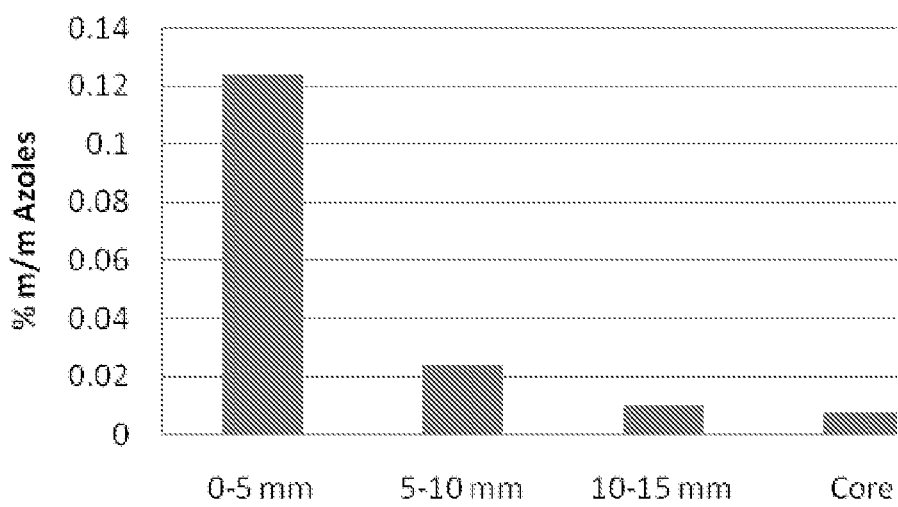
FIG. 2 is an example of the gradient obtained by chemical analysis of Example 1d. It reveals that for the treated wood specimens, propiconazole and tebuconazole were readily detected in the core of the specimens treated.

Chemical analysis of treated wood specimens for propiconazole and tebuconazole revealed that the azoles were readily detected in the core of the specimens treated. An example of the gradient obtained by chemical analysis is shown in FIG. 2.

Example 1e

In another example, the proportion of water to miscible co-solvent was altered (increased), as per the Table below.

| Component | % w/w |
|---|---|
| Wolman ® AG concentrate | 9.0 |
| Ethylene glycol | 30.0 |
| Water | 50.0 |
| Azole marker (proprietary) | Balance |

Substrate: Kiln dried radiata pine sapwood (rougher headed), 90×35 mm. Ten replicates, end sealed.
Treatment: Flood, +60 kPa (1 min), drain, vacuum (−85 kPa, 15 min).
Mean uptake: 67.2 L/m$^3$.
Moisture content: 21.8%

Some samples from these treatments were selected for analysis. The results are summarised in the Table 3, below. These results indicate adequate penetration of the core was achieved.

TABLE 3

Data obtained from Example 1e

| Sample No. | Uptake (L/m$^3$) | Total Azole Analysis (% m/m) Cross-section | Inner 1/9$^{th}$ |
|---|---|---|---|
| 1e(i) | 54.6 | 0.095 | 0.042 |
| 1e(ii) | 62.2 | 0.088 | 0.053 |
| 1e(iii) | 75.2 | 0.135 | 0.103 |

Example 1f

The azoles propiconazole and tebuconazole are quite soluble in ethylene glycol. To ensure that the efficacy of the preservative was not compromised through enhanced leaching of the azoles, an accelerated leaching study was carried out. Matched specimens treated with Vacsol® Azure, a commercial light organic solvent preservative (LOSP) than contains the same actives, were included for comparison. The method involved cutting two adjacent 10 mm sections from the middle of each specimen. One section was set aside as an unleached control, the other was leached in accordance with the method outlined in the *Protocols of the Australasian Wood Preservation Committee* (March 2007 Revision, see, www.t-paa.com.au) for termite or fungal bioassays (i.e., shaking water-bath, 7 days, daily changes of water). At the completion of the leaching, the specimens were dried and along with the unleached control, analysed for azoles. The results indicated that the leaching of azoles from timber treated with the reduced drying formulation was similar to that from timber treated with Vacsol® Azure. On average, 87% of azoles were retained from the Wolman® AG/ethylene glycol treatment, and 83% from the Vacsol® Azure control. A fungal bioassay in the form of a soil block test was also undertaken, and for a given azole retention, the results indicated that the anti-fungal effectiveness of the Wolman® AG/ethylene glycol formulation was comparable to the commercially used LOSP, Vacsol® Azure.

Examples of Envelope Penetration

Example 2a

This example demonstrates reduced moisture content (MC) increase and reduced swelling Preservative: Permethrin, emulsifiable concentrate (0.5% w/w)
Carrier: Various, refer to Table 4, below
Substrate: Radiata pine, 90×35 mm, sets of ten, matched specimens
Treatment: Dipping

TABLE 4

Data obtained from Example 2a

| Carrier | Carrier Ratio (v/v) | Mean uptake (L/m$^3$)$^a$ | MC after treatment (%)$^b$ | MC increase | Volumetric swelling (%)$^b$ |
|---|---|---|---|---|---|
| Water only | — | 16.3 | 18.6 | 8.0 | 1.5 |
| Water/ethylene glycol | 50/50 | 12.7 | 14.6 | 3.7 | 0.81 |
| Water/propylene glycol | 50/50 | 12.8 | 12.6 | 1.7 | 0.72 |
| Water/ethylene glycol/glycerol | 40/50/10 | 12.7 | 13.0 | 1.5 | 0.60 |
| Tanalith ® T (reference) | — | 10.0 | 10.0 | — | — |

$^a$Mean of ten replicates;
$^b$24 hours after treatment

Example 2b

This example demonstrates envelope formation from reduced drying carrier systems. Envelope formation demonstrated by chemical analysis of the outer zone (0-2.5 mm) and the inner zone (2.5-5.0 mm).

Preservative: Permethrin, emulsifiable concentrate (0.5% w/w)
Carrier: Various, refer to Table below
Substrate: Radiata pine, 90×35 mm, sets of ten, end-sealed matched specimens
Treatment: Dipping

TABLE 5

Data obtained from Example 2b

| Carrier | Carrier Ratio (v/v) | Mean uptake (L/m$^3$)$^a$ | Mean permethrin retention (% m/m)$^b$ |
|---|---|---|---|
| Water/ethylene glycol n-butyl ether | 60/40 | 22.2 | 0.062/0.018 |
| Water/ethylene glycol | 50/50 | 19.1 | 0.054/0.008 |
| Water/ethylene glycol/ethylene glycol n-butyl ether/WD Alkyd$^c$ | 50/33/5/12 | 21.1 | 0.071/0.011 |

$^a$Mean of ten replicates;
$^b$Retentions correspond to outer (0-2.5 mm) and inner (2.5-5.0 mm) zones, respectively;
$^c$WD Alkyd = water dispersible alkyd resin.

Example 2c

This example demonstrates various formulations within the scope of the present invention. For example, permethrin, in the form of an emulsifiable concentrate, can be dissolved in water, and ethylene glycol added to give stable formulations for the treatment of timber. The ratio of water to co-solvent can be varied without impacting on stability.

| Component | Sample 2c(i) % w/w | Sample 2c(ii) % w/w |
| --- | --- | --- |
| Permethrin | 0.50 | 0.50 |
| Emulsifier system | 0.50 | 0.50 |
| Ethylene glycol | 49.5 | 25 |
| Water | 49.5 | 74 |

In some instances, emulsifiers are not required for water insoluble actives. The following formulation is surprisingly stable, and useful for envelope treatments of timber to protect against insect attack.

| Component | Sample 2c(iii) % w/w |
| --- | --- |
| Permethrin | 0.50 |
| Butyl oxitol | 9.5 |
| Ethylene glycol | 40 |
| Water | 50 |

Example 2d

To demonstrate the efficacy of a preservative in one of the inventive carrier systems, a field trial was undertaken. The scope of the field trial is summarised in the Table below.

In this field trial, permethrin, in the form of an emulsifiable concentrate was blended in a 50/50 mixture of water and ethylene glycol. This formulation was used to treat the timber specimens, which were subsequently exposed to the subterranean termite *Coptotermes acinaciformis* in the field. To test the efficacy of the envelope formed by the inventive formulation, a field trial was carried out by the Commonwealth Scientific and Industrial Research Organisation (CSIRO, Australia), in accordance with the *Protocols for Assessment of Wood Preservatives*. The experimental details of the trial are summarised in Table 6. The field trial specimens were treated in 200 mm lengths. Sections of the leftover material were retained, and submitted to the Chemical Laboratory at Department Primary Industries and Fisheries, Queensland, Australia, for chemical analysis. The results are given in Table 7, below. Zone analysis was also undertaken to confirm formation of the 5 mm penetration zone.

TABLE 6

Summary of details of CSIRO field trial

| | |
| --- | --- |
| Research provider | CSIRO |
| Permethrin envelope retention | 0.02% m/m (outer 5 mm) |
| Carrier system | Water/ethylene glycol |
| Controls | Untreated & water/glycol control |
| Reference preservative | Tanalith ® T (permethrin 0.02% m/m) & oil/kerosene control |
| Substrate | Pinus radiata sapwood |
| Specimen size | 200 × 90 × 45 mm |
| Treatment | Dip |
| Retention verification | Chemical analysis |
| End seal | Specimens were cut from 400 mm lengths of treated pine and end sealed with a momentary dip in the treatment solution |
| Specimen pre-conditioning | Outdoor exposure (1 month) at Clayton, vacuum-oven drying (5 days) |
| Replication | 6 |
| Field trial site | Gunn Point, Northern Territory |
| Trial method | Drum technique |
| Duration of trial | 12 months |
| Termite species present | C. acinaciformis |
| Method of assessment | Visual assessment using CSIRO rating system. |
| | 8—Sound |
| | 7—Superficial attack or grazing by termites |
| | 6—Surface attack to a depth exceeding treatment envelope |
| | 5—Attack (slight) 10-25% mass loss |
| | 4—Attack (moderate) 25-50% mass loss |
| | 3—Attack (heavy) 50-75% mass loss |
| | 2—Attack (severe) 75-90% mass loss |
| | 1—Attack (destroyed) >90% mass loss |

TABLE 7

Summary of results for Example 2d

| Treatment formulation (active ingredient) | Mean mass loss (%)$^a$ (standard error) | Mean rating$^a$ | Range |
| --- | --- | --- | --- |
| Untreated (control) | 90.1 (2.9) | 1.2 | 1-2 |
| Permethrin in water/ethylene glycol | 0.8 (0.1) | 7.8 | 7-8 |
| Tanalith ® T Solvent (control) | 69.4 (7.9) | 1.8 | 1-4 |
| Tanalith ® T (permethrin) | 0.2 (0.0) | 8.0 | 8-8 |

$^a$Means of six replicates

After exposure in the field for approximately 12 months, the specimens treated with permethrin in the water/ethylene glycol carrier were sound, having achieved a mean rating of 7.8 (maximum=8). The results are summarised in Table 6, below. In contrast, the untreated controls had been heavily attacked, the latter having a mean rating of 1.2. The reference preservative specimens had a mean rating of 8.0. The results demonstrate that permethrin, delivered from the inventive carrier system, is equally efficacious as the reference preservative, Tanalith® T, which contains permethrin in an oil/kerosene mixture (an accepted industry standard).

Example 2e

This example demonstrates various inventive reduced drying carriers (glycerol as well as ethylene glycol). It further shows that different carriers were stable, and the different ratios of carriers facilitate different uptakes. End sealed, matched sets of ten replicates of radiata pine sapwood (90×35 mm) were dip treated in various reduced drying carriers containing permethrin in the form of an emulsifiable concentrate (permethrin concentration ~5 g/L). The formulations were stable, in that no sediment or separation occurred over a period of four weeks at ambient temperature. The mean uptakes of the treatments are shown Table 8, below.

TABLE 8

Data obtained from Example 2e

| Carrier | Stability | Carrier Ratio (v/v) | Mean uptake (L/m$^3$) |
| --- | --- | --- | --- |
| Water | Stable | — | 19.8 |
| Water/ethylene glycol | Stable | 90/10 | 19.8 |
| Water/ethylene glycol | Stable | 75/25 | 18.8 |
| Water/ethylene glycol | Stable | 50/50 | 17.7 |
| Water/glycerol | Stable | 90/10 | 19.0 |
| Water/glycerol | Stable | 75/25 | 15.2 |
| Water/glycerol | Stable | 50/50 | 9.3 |

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Thus, while there has been described what are believed to be the preferred embodiments of the invention, those skilled in the art will recognise that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

It will be appreciated that wood treated according to the present invention may be characterised by a "dry after" requirement for treated timber, having less than 15% moisture content, whilst achieving the required penetration of active compounds into the wood.

It will be further appreciated that the present invention provides for a material for treating wood that has relatively low odour, relatively minimal VOC emissions, and relatively less reliance on mineral spirits, whilst at once providing relatively good dimensional stability to the treated wood.

The claims defining the invention are as follows:

1. A carrier formulation for operatively supporting a preservative or preservative mixture for treating wood, said carrier formulation comprising:
   water; and
   one or more water-miscible compounds including glycols or glycol ethers; and
   a non-water miscible wood preservative;
   wherein said carrier formulation provides for preservative penetration and substantial preservative retention within the treated wood; and
   wherein said carrier formulation provides for treated wood that requires relatively reduced drying.

2. A carrier formulation according to claim 1, further comprising one or more water-miscible compounds selected from the group consisting of: glycerol, propylene glycol, ethylene glycol, amine oxides, quaternary ammonium compounds, esters, alcohols, phenols, diols, triols, ketones, carbamates, amides, sulfoxides, amines, acids, modified cellulosics or the like, or combinations thereof, polymer/resins, PEGs, water dispersible alkyds, polyesters, proteins, and mixtures thereof.

3. A carrier formulation according to claim 1, wherein said one or more water-miscible compounds are ethylene glycol or propylene glycol.

4. A carrier formulation according to claim 1, wherein the ratio of water to one or more water-miscible compounds present in the carrier is within the range of about 1:99 to about 99:1 w/w.

5. A carrier formulation according to claim 1, wherein the ratio of water to one or more water-miscible compounds present in the carrier is within the range of about 20:80 to about 80:20 w/w.

6. A carrier formulation according to claim 5, wherein the ratio of water to one or more water-miscible compounds present in the carrier is within the range of about 40:60 to about 60:40 w/w.

7. A carrier formulation according to claim 1, wherein the uptake of said carrier by said wood is less than 200 L/m$^3$.

8. A carrier formulation according to claim 7, wherein the uptake of said carrier by said wood is less than 80 L/m$^3$.

9. A carrier formulation according to claim 8, wherein the uptake of said carrier by said wood is in the range of about 5 to 30 L/m$^3$.

10. A carrier formulation according to claim 1, wherein the formulation is applicable to wood composites selected from the group consisting of: particle board, plywood, medium density fibreboard (MDF) and oriented strand board (OSB).

11. A carrier formulation according to claim 1, wherein said one or more water-miscible compounds comprise glycols and alcohols.

12. A carrier formulation according to claim 11, wherein said one or more water-miscible compounds comprise monoethylene glycol (MEG), monoethanol amine (MEA) and polyethylene glycol (PEG).

13. A carrier formulation according to claim 1, comprising below about 5% w/w preservative content.

14. A carrier formulation according to claim 1, comprising below about 2% w/w preservative content.

15. A carrier formulation according to claim 14, comprising below about 1% w/w preservative content.

16. A carrier formulation according to claim 1, wherein said preservative or preservative mixture is selected from the group consisting of: insecticides, termiticides, fungicides, mouldicides, and mixtures thereof.

17. A carrier formulation according to claim 1, wherein said preservative or preservative mixture is selected from the group consisting of: synthetic pyrethroids (selected from allethrin, bifenthrin, cypermethrin, cyphenothrin, deltamethrin, permethrin, prallethrin, resmethrin, sumithrin, tetramethrin, tralomethrin, transfluthrin, and imiprothrin), triazoles, triazoles, copper azole-based compounds, organic biocides, thiachloprid, imidachloprid, and mixtures thereof, triazoles, copper azole-based compounds, organic biocides, iodopropynylbuthylcarbamate (IPBC), organic tin compounds such as tributyltin naphthenate (TBTN), organic copper compounds such as copper 8 quinolinolate, copper naphthenate, organic zinc compounds, quaternary ammonium compounds, tertiary ammonium compounds, isothiazolones, boron compounds, 3-benzothien-2-yl-5,6-dihydro-1,4,2-oxathiazine-4-oxide and bis-(N-cyclohexyldiazenuimdioxy) copper ("Cu—HDO") and mixtures thereof.

18. A carrier formulation according to claim 1, wherein said preservative or preservative mixture is bifenthrin, permethrin, tebuconazole, propiconazole, or cyproconazole or a combination thereof.

19. A carrier formulation according to claim 1, wherein said preservative or preservative mixture is copper naphthenate, copper oxine (copper 8 quinolate), or a mixture thereof.

20. A carrier formulation according to claim 1, wherein said preservative or preservative mixture is selected from the group consisting of: organochlorine compounds, organophosphates, neonicotinoids and biological insecticides.

21. A carrier formulation according to claim 20, wherein said neonicotinoids are selected from the group consisting of:

acetamiprid, clothianidin, dinotefuran, imidacloprid, nitenpyram, thiacloprid, thiamethoxam and mixtures thereof.

22. A carrier formulation according to claim 1, comprising one or more azole compounds in a carrier formulation of water/monoethylene glycol.

23. A carrier formulation according to claim 22, having an uptake of about 60 L/m$^3$.

24. A method of treating wood, said method comprising the step of contacting said wood with a carrier formulation defined according to claim 1.

* * * * *